(12) United States Patent
Durocher

(10) Patent No.: US 8,551,774 B2
(45) Date of Patent: Oct. 8, 2013

(54) EXPRESSION VECTORS CONTAINING A TRUNCATED EPSTEIN BARR NUCLEAR ANTIGEN 1 LACKING THE GLY-GLY-ALA DOMAIN FOR ENHANCED TRANSIENT GENE EXPRESSION

(75) Inventor: Yves Durocher, Montreal (CA)

(73) Assignee: National Research Council of Canada, Ottawa, Ontario (CA)

( * ) Notice: Subject to any disclaimer, the term of this patent is extended or adjusted under 35 U.S.C. 154(b) by 188 days.

(21) Appl. No.: 11/576,005

(22) PCT Filed: Mar. 17, 2006

(86) PCT No.: PCT/CA2006/000403
§ 371 (c)(1),
(2), (4) Date: Mar. 26, 2007

(87) PCT Pub. No.: WO2006/096989
PCT Pub. Date: Sep. 21, 2006

(65) Prior Publication Data
US 2008/0070232 A1    Mar. 20, 2008

Related U.S. Application Data

(60) Provisional application No. 60/662,392, filed on Mar. 17, 2005.

(51) Int. Cl.
*C12N 15/85* (2006.01)
*C12N 15/63* (2006.01)

(52) U.S. Cl.
USPC ........ 435/325; 435/70.1; 435/455; 435/320.1

(58) Field of Classification Search
None
See application file for complete search history.

(56) References Cited

U.S. PATENT DOCUMENTS 6,417,002 B1 * 7/2002 Horlick et al. ................ 435/455

FOREIGN PATENT DOCUMENTS

WO    02/090533 A2    11/2002
WO    WO/2004/007536 A2 *    1/2004

OTHER PUBLICATIONS

Durocher et al (Nucleic Acid Research, 2002, vol. 30, p. 1-9).*
Wu et al. (Journal of Virology, 2002, vol. 76, p. 2480-2490.*
Durocher (Nucleic Acid Research, 2002, vol. 30, p. 1-9) of record on Feb. 9, 2009.*
Promega Technical reference 2010 p. 1.*
Mackey David et al: "The linking regions of EBNA1 are essential for its support of replication and transcription" Molecular and Cellular Biology, vol. 19, No. 5 May 1999, pp. 3349-3359.
Ceccarelli Derek F J et al: "Functional analyses of the EBNA1 origin DNA binding protein of Epstein-Barr virus" Journal of Virology, vol. 74, No. 11, Jun. 2000, pp. 4939-4948.
Goldsmith Kim et al: "Identification of EBNA1 amino acid sequences required for the interaction of the functional elements of the Epstein-Barr virus latent origin of DNA replication" Journal of Virology, vol. 67, No. 6, 1993, pp. 3418-3426.

(Continued)

*Primary Examiner* — Agnieszka Boesen
(74) *Attorney, Agent, or Firm* — Browdy and Neimark, PLLC

(57) ABSTRACT

This invention relates to the unexpected discovery that nucleotide coding sequences coding for a truncated Epstein Barr Nuclear Antigen 1 (EBNA1t) protein (lacking the Gly-Gly-Ala domain), when in cells of mammalian origin, are associated with improved growth and increased transient gene expression when compared with cells expressing a complete EBNA1 coding sequence. The expression of EBNA1t also appear to be more stable over time.

3 Claims, 16 Drawing Sheets

Transient co-expression of truncated EBNA1 (EBNA1t) significantly enhance protein expression in 293F cells

(56) References Cited

OTHER PUBLICATIONS

European patent application No. 06721674.7: search report dated Jun. 24, 2009.
Wurm and Bernard "large-scale transient expression in mammalian cells for recombinant protein production" Curropin. Biotechnol. 10:156-159 (1999).
Pham et al.,"Large-scale transfection of mammalian cells for the fast production of recombinant protein" Mol. Biotechnol. 34:225-237 (2006).
Stedman's Medical Dictionary, 26th Edition, Williams and Wilkins, Baltimore, Maryland, 1995, p. 978.
Wendelburg et al., "An enhanced EBNA1 variant with reduced IR3 domain for long-term episomal maintenance and transgene expression of oriP-based plasmids in human cells" Gene Therapy 5:1389-1399 (1998).
Yates et al.,"Dissection of DNA Replication and Enhancer Activation Functions of Epstein-Barr Virus Nuclear Antigen 1" Cancer Cells. 6:197-205 (1988).
Patel et al. "Expression of the Epstein-Barr Virus Encoded EBNA-I Gene in Stably Transfected Human and Murine Cell Lines" Int. J. Cancer: vol. 42, 592-598 (1988).
Yates et al.,"Stable replication of plasmids derived from Epstein-Barr virus in various mammalian cells" Nature, vol. 313, p. 912 (1985).
Kirchmaier et al. "Dominant-Negative Inhibitors of EBNA-I of Epstein-Barr Virus" Journal of Virology, vol. 71(3) pp. 1766-1775 (1997).
European Office Action dated Jan. 7, 2011, regarding European Application No. 06721674.7-1212.

\* cited by examiner

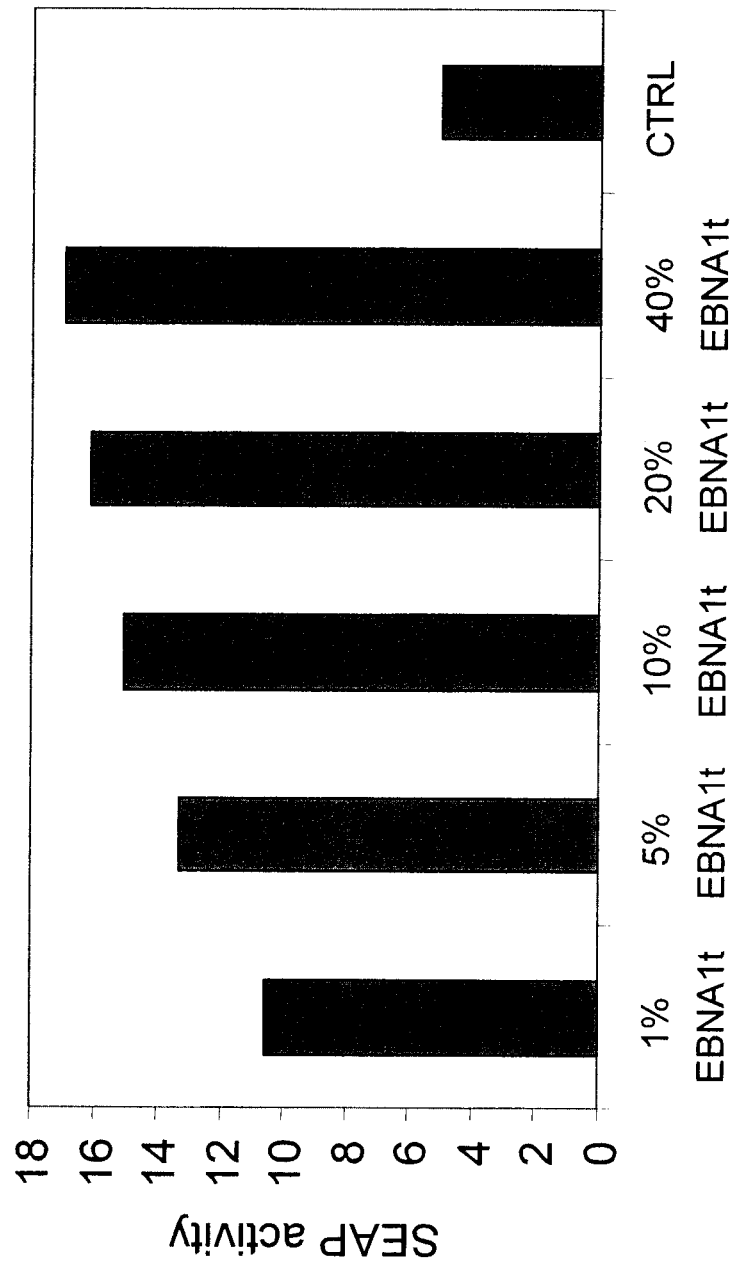
Figure 1: Transient co-expression of truncated EBNA1 (EBNA1t) significantly enhance protein expression in 293F cells

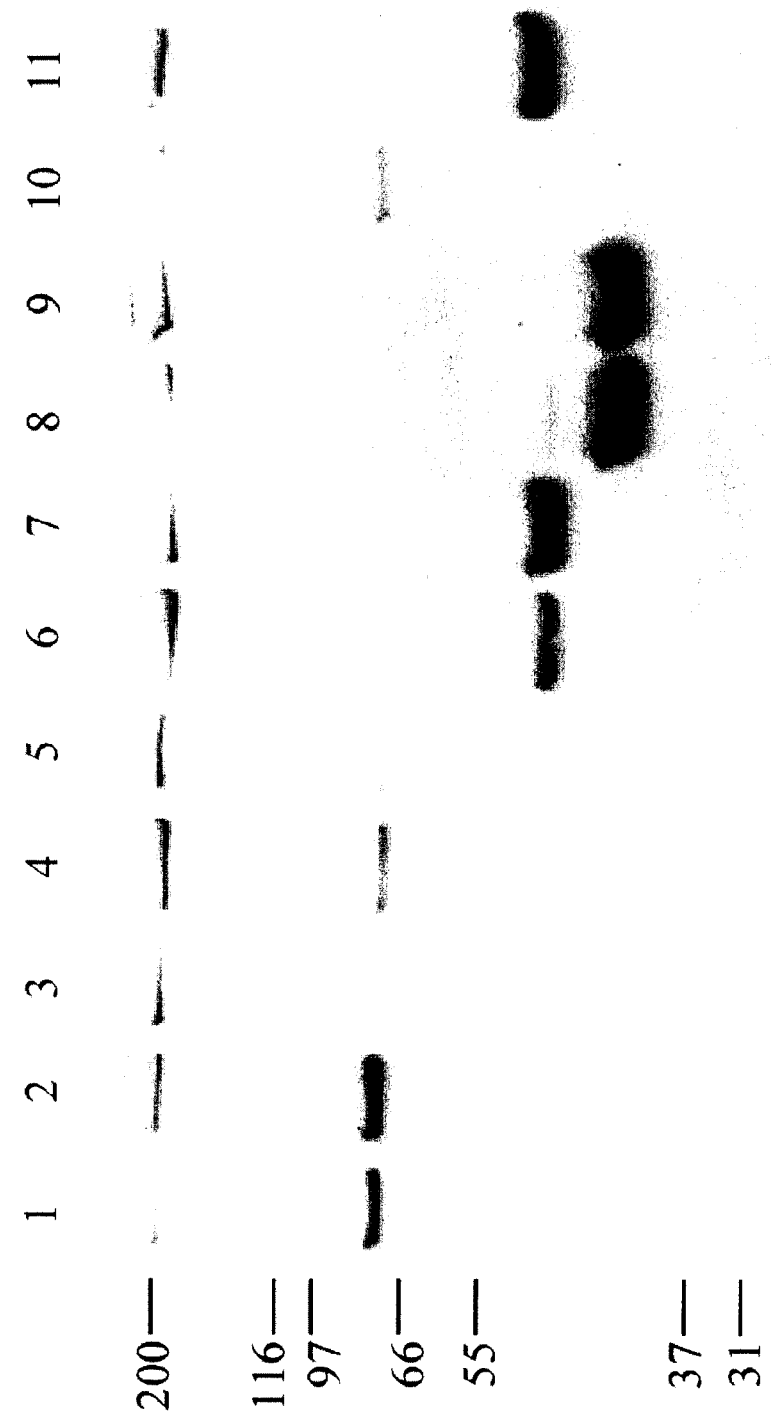
Figure 2: EBNA1 expression HEK293 cells

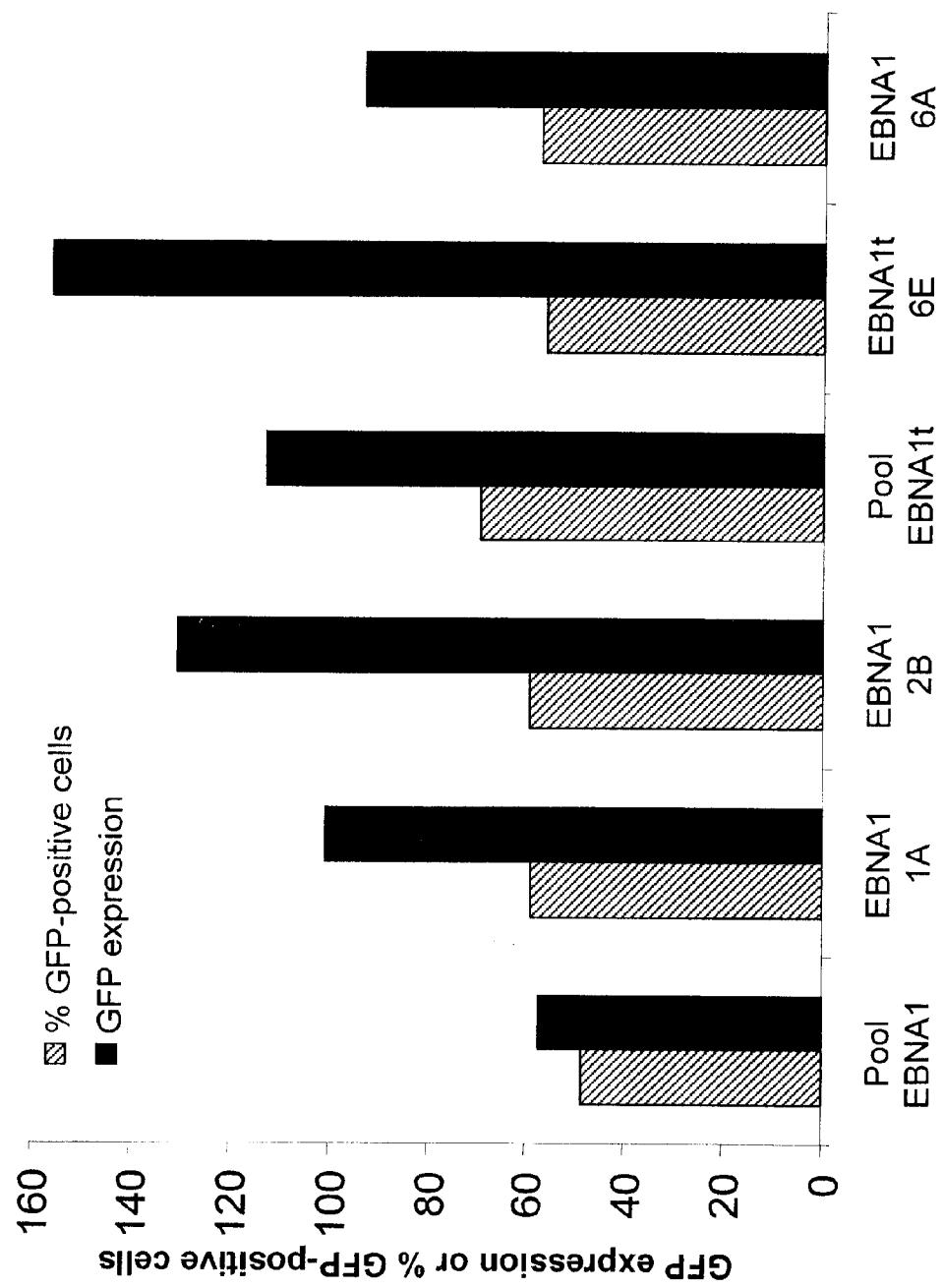
Figure 3: GFP expression following transient transfection of various 293F-EBNA1 cells

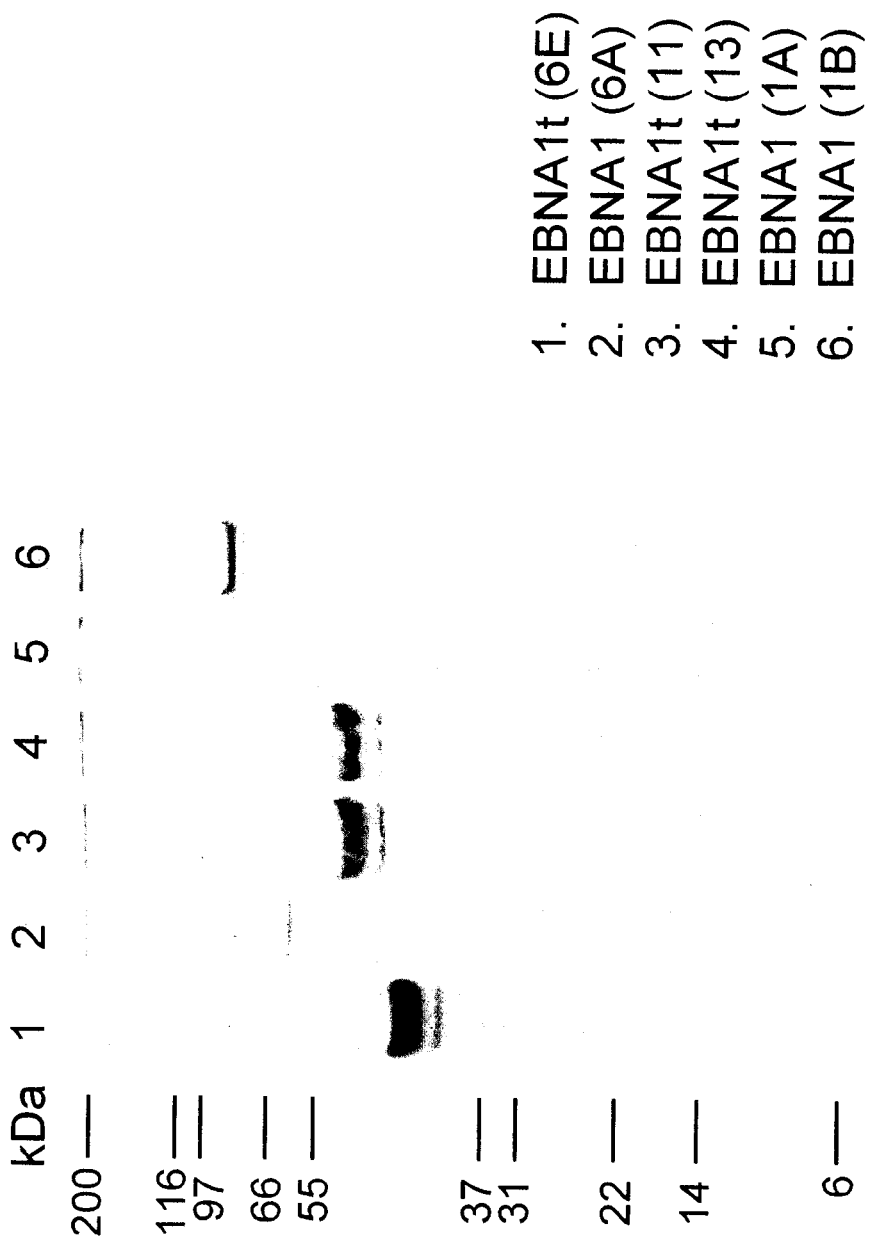
Figure 4: EBNA1 expression in various 293F clones

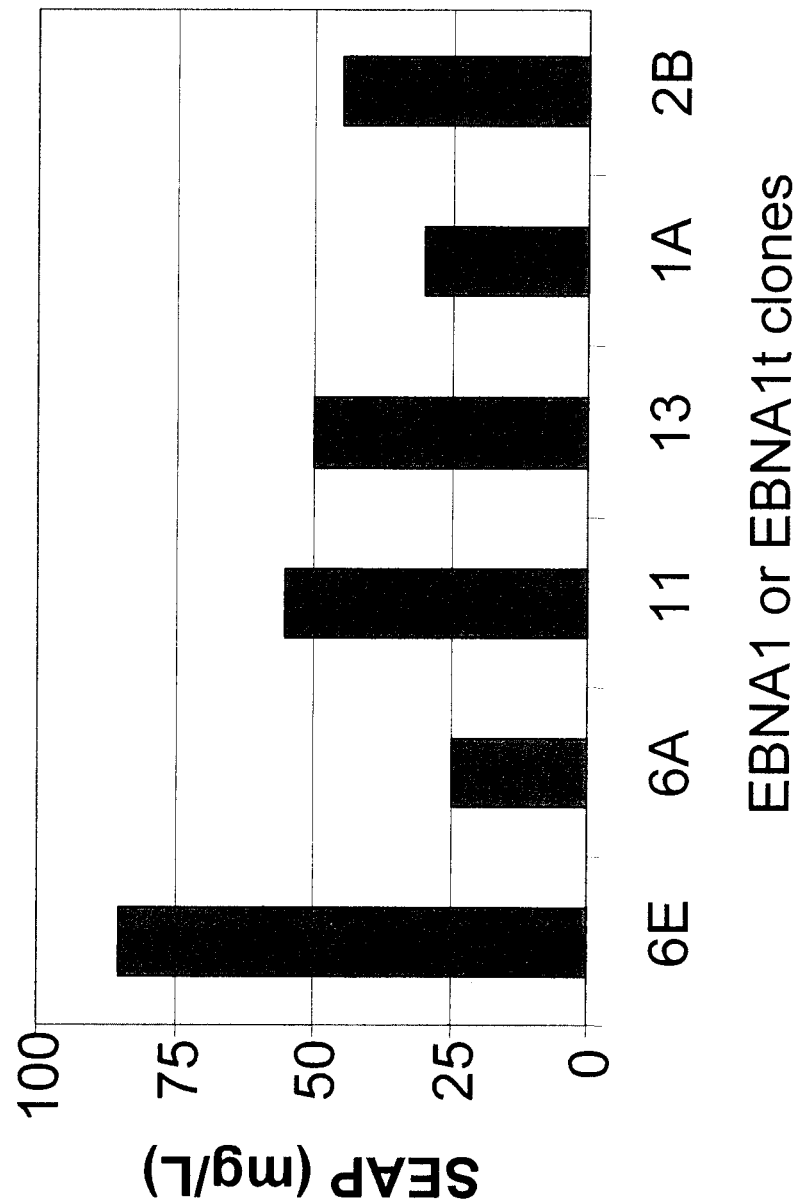
Figure 5: Transient SEAP expression in various 293F-EBNA1 clones.

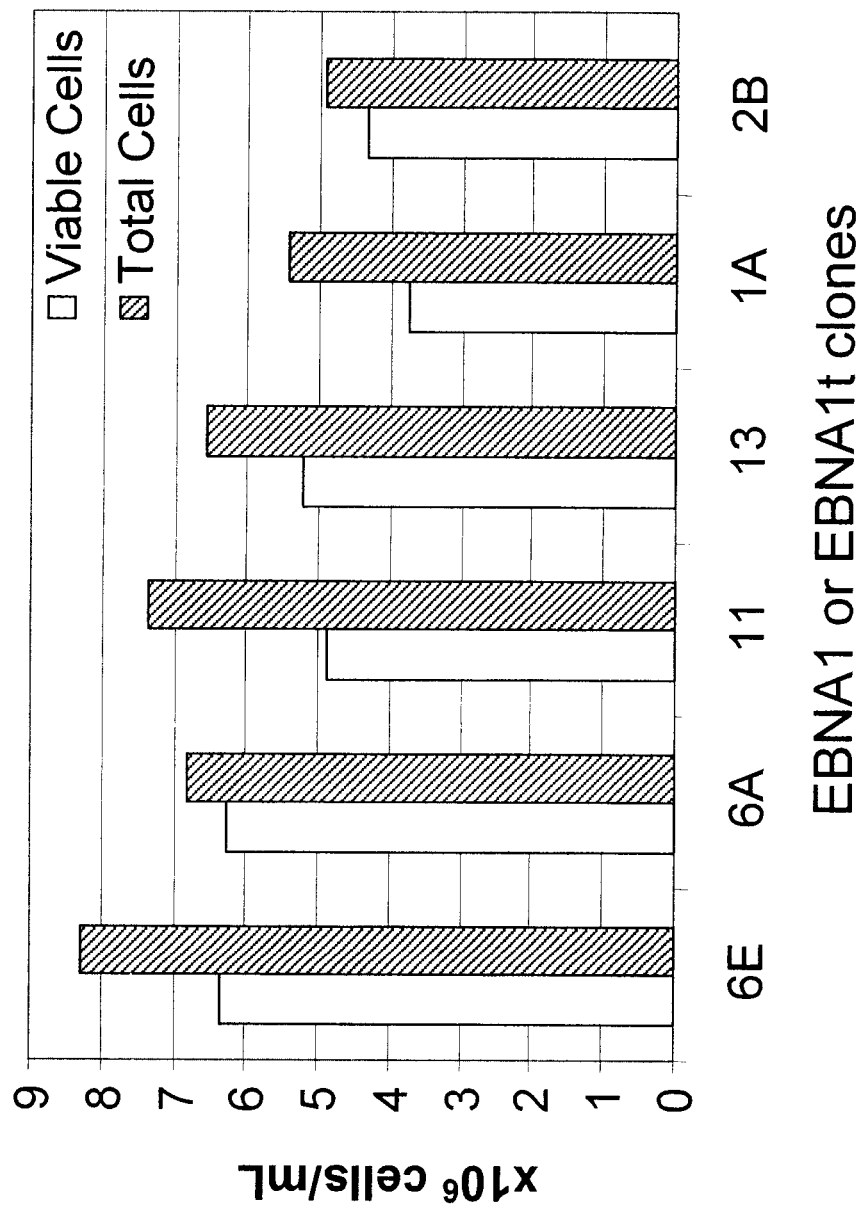
Figure 6: Growth of various 293F-EBNA1 clones measured at 144 hpt.

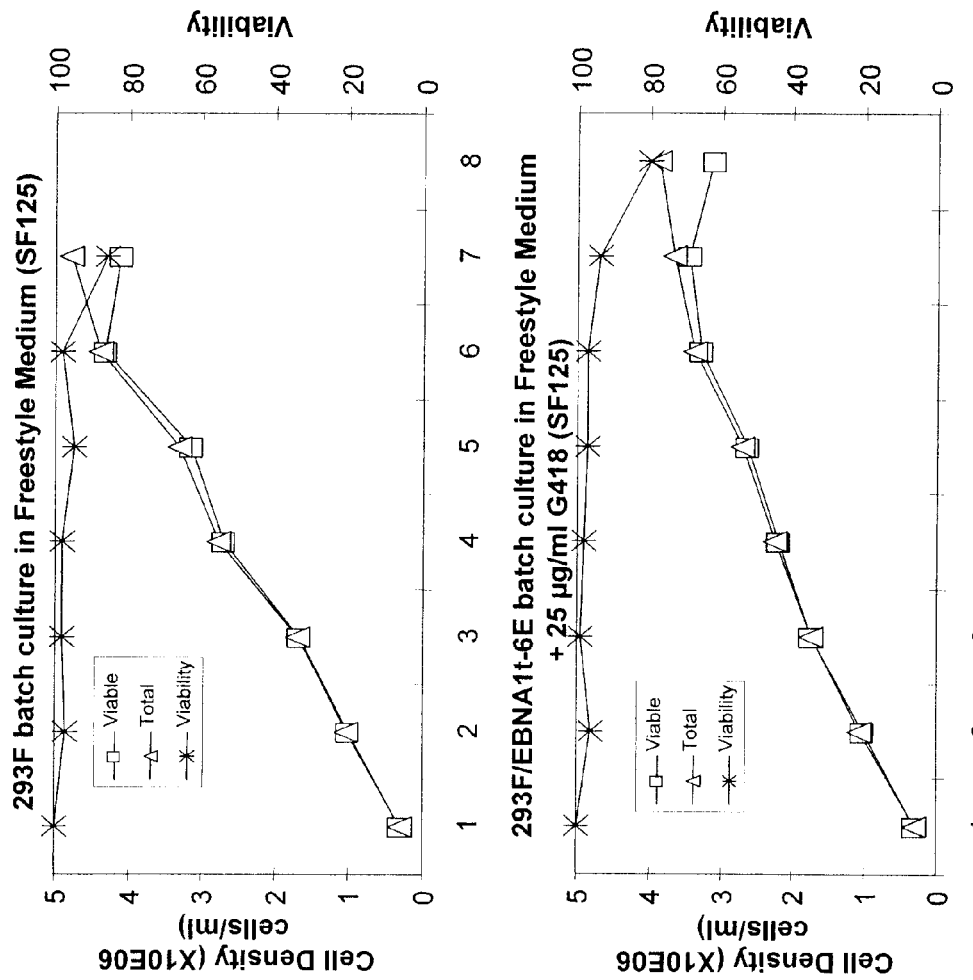
Figure 7: Growth characteristics of 293F (upper panel) and 293FEt (clone 6E, lower panel) cell lines in Freestyle medium.

Fig 8: EBNA1 amino acid sequence
Accession number : NC_001345

```
  1  MSDEGPGTGP GNGLGEKGDT SGPEGSGGSG PQRRGGDNHG RGRGRGRGRG GRPGAPGGS
 61  GSGPRHRDGV RRPQKRPSCI GCKGTHGGTG AGAGAGGAGA GGAGAGGGAG AGGGAGGAGG
        Transcription(65-89)            Linking Region 1 (33-89)
121  AGGAGAGGGA GAGGAGGAG GAGAGGGAGA GGGAGGAGAG AGGGAGGAGA GGAGAGGAGG
                              Gly-Gly-Ala Repeats (90-327)
181  AGGAGAGGGA GAGAGGAGGA GGAGAGGAGA AGGGAGGAGA GGGAGGAGGA GAGGAGAGGA
241  GAGGAGAGGA AGAGGAGGAG AGGGAGGAGA GGGAGGAGAG GGGAGGAGA GAGGAGAGGA
301  GGAGAGGAGG AGAGGGAGAG GAGAGGGGAG RGGSGGGRGRG GSGGRGRGRG GGRRGRGRER
361  ARGGSRERAR GRGRGRGEKR PRSPSSQSSS SGSPPRRPPP GRRPFFHPVG EADYFEYHQE
                               NLS (379-386)         Linking Region 2 (328-378)
421  GGPDGEPDVP PGAIEQGPAD DPGEGPSTGP RGQGDGGRRK KGGWFGKHRG QGGSNPKFEN
481  IAEGLRALLA RSHVERTTDE GTWVAGVFVY GGSKTSLYNL RRGTALAIPQ CRLTPLSRLP
541  FGMAPGPGPQ PGPLRESIVC YFMVFLQTHI FAEVLKDAIK DLVMTKPAPT CNIRVTVCSF
                Dimerization & DNA binding (458-641)
601  DDGVDLPPWF PPMVEGAAAE GDDGDDGDEG GDGDEGEEGQ E
```

Fig 9: EBNA1, EBNA1t & EBNA1c

```
  1  MSDEGPGTGP GNGLGEKGDT SGPEGSGGSG PQRRGGDNHG RGRGRGRGRG GGRPGAPGGS
 61  GSGPRHRDGV RRPQKRPSCI GCKGTHGGTG AGAGAGGAGA GGAGAGGGAG AGGGAGGAGG
121  AGGAGAGGGA GGAGGAGGAG GAGAGGAGAG GGAGGAGGAG AGGGAGGAGA AGGGAGGAGG
181  AGGAGAGGGA GGAGGAGGAG GGAGGAGGAG AGGGAGGAGA GGGAGGAGGA GAGGAGAGGA
241  GAGAGGAGGA GGAGGAGGAG AGGGAGGAGA AGGGAGGAGA GGGAGGAGAG GAGGAGAGGA
301  GGAGAGGAGG AGAGGGAGAG GAGAGGGGRG RGGSGGRGRG GSGGRGRGRG GGRRGRGRER
                                            M
361  ARGGSRERAR GRGRGRGEKR PRSPSSQSSS SGSPPRRPPP GRRPFFHPVG EADYFEYHQE
421  GGPDGEPDVP PGAIEQGPAD DPGEGPSTGP RGQGDGGRRK KGGWFGKHRG QGGSNPKFEN
481  IAEGLRALLA RSHVERTTDE GTWVAGVFVY GGSKTSLYNL RRGTALAIPQ CRLTPLSRLP
541  FGMAPGPGPQ PGPLRESIVC YFMVFLQTHI FAEVLKDAIK DLVMTKPAPT CNIRVTVCSF
601  DDGVDLPPWF PPMVEGAAAE GDDGDDGDEG GDGDEGEEGQ E
```

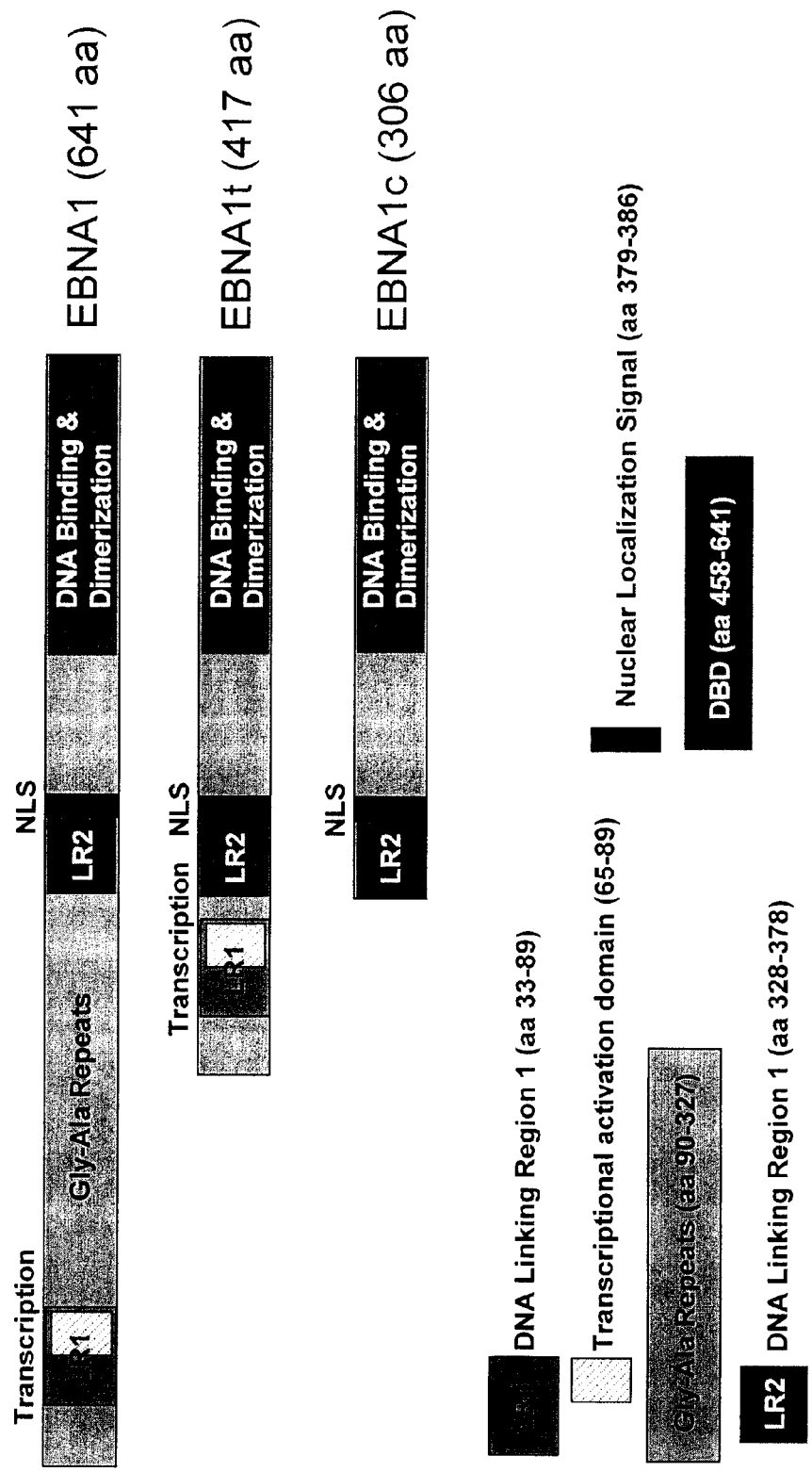
Fig 10: Schematic structure of EBNA1 constructs

Fig 11A: EBNA1 DNA sequence

```
   1  atgtctgacg agggccagg  tacaggacct ggaaatggcc taggagagaa gggagacaca tctggaccag
  71  aaggctccgg cggcagtgga cctcaaagaa gaggggtga  taaccatgga cgaggacggg gaagaggacg
 141  aggacgagga ggcggaagac caggagcccc ggcggctca  gatcagggc  caagacatag agatgtgtc
 211  cggagacccc aaaaacgtcc aagttgcatt ggctgcaaag ggacccacgg tggaacagga gcaggagcag
 281  gagcgggagg ggcaggagca ggaggggcag gagcaggagg agggcagga  gcaggaggag gggcaggagg
 351  ggcaggaggg gcaggaggag caggaggagg ggcaggagca agaggggca  gaggcagga  agggcagga
 421  ggggcaggag caggaggagg ggcaggagca gcaggaggag caggagggg  caggagggc  ggagcaggag
 491  gaggcaggag agggcaggag ggagggcag  gcaggaggc aggaggagg ggcaggaggg caggagcagg
 561  agcaggggca ggaggggcag gcaggagga  agcaggagga gggcaggag agcaggggc  aggagggca
 631  ggaggggcag gagcaggagg ggcaggagca gaggaggagg gggcaggag  aggagggca  ggagcaggag
 701  gggcaggagc aggaggggca ggagcaggag gggcaggagc aggagggca  ggaggaggag gagcaggag
 771  ggcaggaggg gcaggaggag gcaggaggag aggggcagga ggggcagga  gggcaggagg ggcaggagca
 841  ggaggagggg caggaggggc aggagcagga ggggcaggag ggggcaggag  agggggca   ggagggcag
 911  gagcaggagg ggcaggagga gcaggagcag gcaggaggc agggcagga  gggcaggag  caggaggtgg
 981  aggccggggt cgaggaggca gtggaggccg gggtcgagga ggtagtggag gccgggtcg aggaggtagt
1051  ggaggccgcc ggggtagagg acgtgaaaga gccaggagtc gaagtcgtga aagagccagg gggagaggtc
1121  gtggacgtgg agaaaagagg cccaggagtc gtcatcatca tccggtctc  cacccgcag
1191  gcccctcca  gtagaaggc  cattttccca cctgtaggg  gaaccgatt  attttgaata ccaccaagaa
1261  ggtggcccag atggtgagcc tgacgtgccc ccgggagcga tagagcaggg ccccgcagat gacccaggag
1331  aaggcccaag cactgaccc  cgggtcagg  gtgatggagg caggcgcaaa aaaggagggt ggtttgaaa
1401  gcatcgtggt caaggaggtt ccaacccgaa atttgagaac attgcaagag gtttaagagc tctcctggct
1471  aggagtcacg tagaaggac  taccgacgaa ggaacttggg tcgccggtgt gttcgtatat ggaggtagta
1541  agacctccct ttacaaccta agcgaggaa  ctgcccttgc tattccacaa tgtcgtctta caccattgag
1611  tcgtctcccc tttggaatgg ccctgacc   cggcccacaa cctgccgcc  taagggagtc cattgtctgt
1681  tatttcatgg tcttttaca  aactcatata tttgctaggg tttgaagga  tgcgattaag gacctgtta
1751  tgacaaagcc cgctcctacc tgcaatatca gggtgactgt gtgcagctgt gacgatggag tagattgcc
1821  tccctggttt ccacctatgg tggaagggc  tgccgcggag ggtgatgacg gagatgacgg agatgaagga
1891  ggtgatggag atgagggtga ggaagggtga gagtga
```

Fig 11B: EBNA1t DNA sequence

```
   1 atgtctgacg aggggccagg tacaggacct ggaaatggcc taggagagaa gggagacaca tctgaccag
  71 aaggctccgg cggcagtgga cctcaaagaa gaggggtga taaccatgga cgaggacggg gaagaggacg
 141 aggacgagga ggcggaagac caggagcccc gggcggctca ggatcaggc caagacatag agatggtgtc
 211 cggagacccc aaaaacgtcc aagttgcatt ggctgcaaag ggaccacgg tggaacagga gcaggagcag
 281 gagcgggagg ggcaggagca ggaggtggag gccggggtcg aggaggcagt ggaggccggg gtcgaggagg
 351 tagtggaggc cggggtcgag gaggtagtgg aggccgccgg gtagaggac gtgaaagagc caggggggga
 421 agtcgtgaaa gagccaggg gagaggtcgt ggacgtggag aaaagaggcc caggagtccc agtagtcagt
 491 catcatcatc cgggtctcca ccgcgcagge ccctccagg tagaaggcca tttttccacc ctgtaggga
 561 agccgattat tttgaatacc accaagaagg tgcccagat ggtgagcctg acgtgcccc gggagcgata
 631 gagcagggcc ccgcagatga cccaggagaa ggcccaagca ctggacccccg gggtcaggg t gatggaggca
 701 ggcgcaaaaa agaggggtgg tttggaaagc atcgtggtca aggaggttcc aacccgaaat ttgagaacat
 771 tgcagaaggt ttaagagctc tcctggctag gagtcacgta gaaaggacta ccgacgaagg aacttgggtc
 841 gccggtgtgt tcgtatatgg agtagtaag acctcccttt acaacctaag gcgaggaact gcccttgcta
 911 ttccacaatg tcgtcttaca ccattgagtc gtctcccctt tggaatggcc cctgacccg gcccacaacc
 981 tggcccgcta agggagtcca ttgtctgtta tttttacaaa ctcatatatt tgctgaggtt
1051 tttgaaggatg cgattaagga cctttgttatg acaaagcccg ctcctacctg caatatcagg gtgactgtgt
1121 gcagctttga cgatggagta gatttgcctc cctgttttcc acctatggtg gaagggctg ccgcggaggg
1191 tgatgacgga gatgacgag atgaaggagg tgatggagat gagggtgagg aagggcagga gtga
```

Fig 11C: EBNA1c DNA sequence

```
  1  atgcggggtc gaggaggtag tggaggccgg ggtcgaggag gtagtggagg ccgccgggt agaggacgtg
 71  aaagagccag gggggaagt cgtgaaagag ccaggggag agtcgtgga cgtggagaaa agaggcccag
141  gagtcccagt agtcagtcat catcatccgg gtctccaccg cgcaggcccc ctccaggtag aaggccattt
211  ttccaccctg taggggaagc cgattattt gaataccacc aagaaggtgg cccagatggt gagcctgacg
281  tgcccccggg agcgatagag caggcccccg cagatgaccc aggagaaggc ccaagcactg gaccccgggg
351  tcagggtgat ggaggcaggc gcaaaaaagg agggtggttt ggaaagcatc gtggtcaagg aggttccaac
421  ccgaaatttg agaacattgc agaaggttta agagctctcc tggctaggag tcacgtagaa aggactaccg
491  acgaaggaac ttgggtcgcc ggtgtgttcg tatatggagg tagtaagacc tccctttaca acctaaggcg
561  aggaactgcc cttgctattc cacaatgtcg tcttacacca ttgagtcgtc tcccctttgg aatgcccct
631  ggaccccggcc cacaacctgg cccgctaagg gagtccattg tctgttattt catgtctttt ttacaaactc
701  atatatttgc tgaggttttg aaggatgcga ttaaggacct tgttatgaca agcccgctc ctacctgcaa
771  tatcagggtg actgtgtgca gctttgacga tggagtagat ttgcctcccct gttttccacc tatggtggaa
841  gggctgccg cggagggtga tgacggagat gacggagatg aaggaggtga tgagatgag ggtgaggaag
911  ggcaggagtg a
```

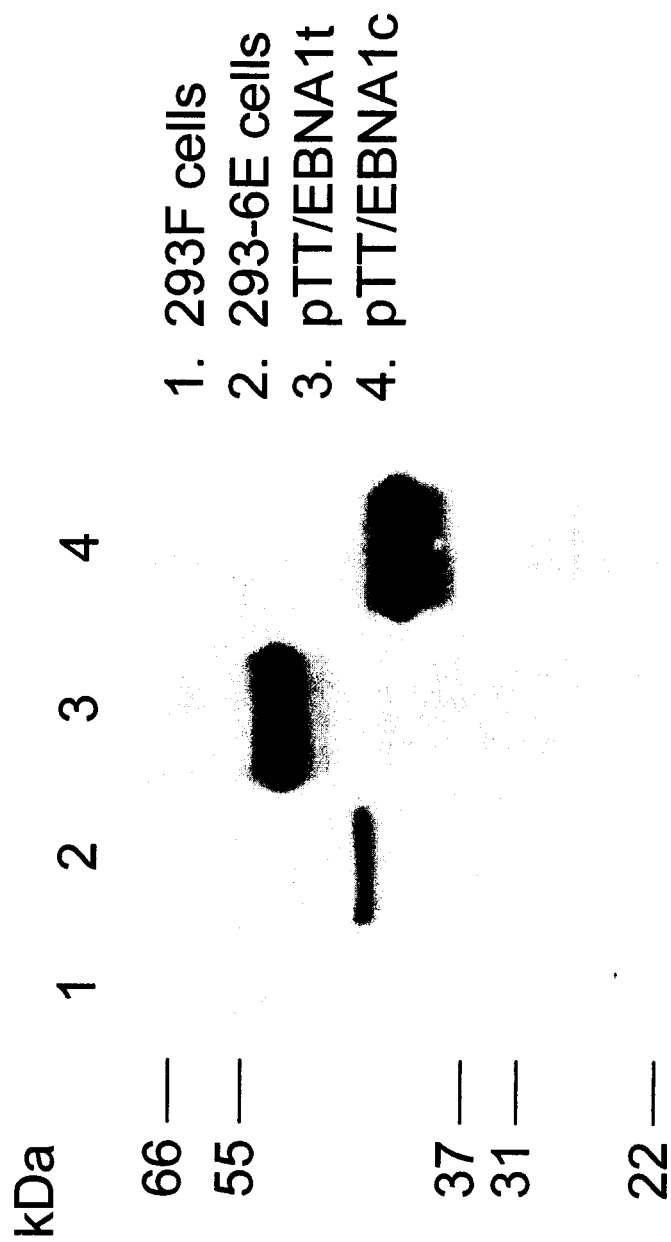
Figure 12: Transient EBNA1t and EBNA1c expression in 293F cells.

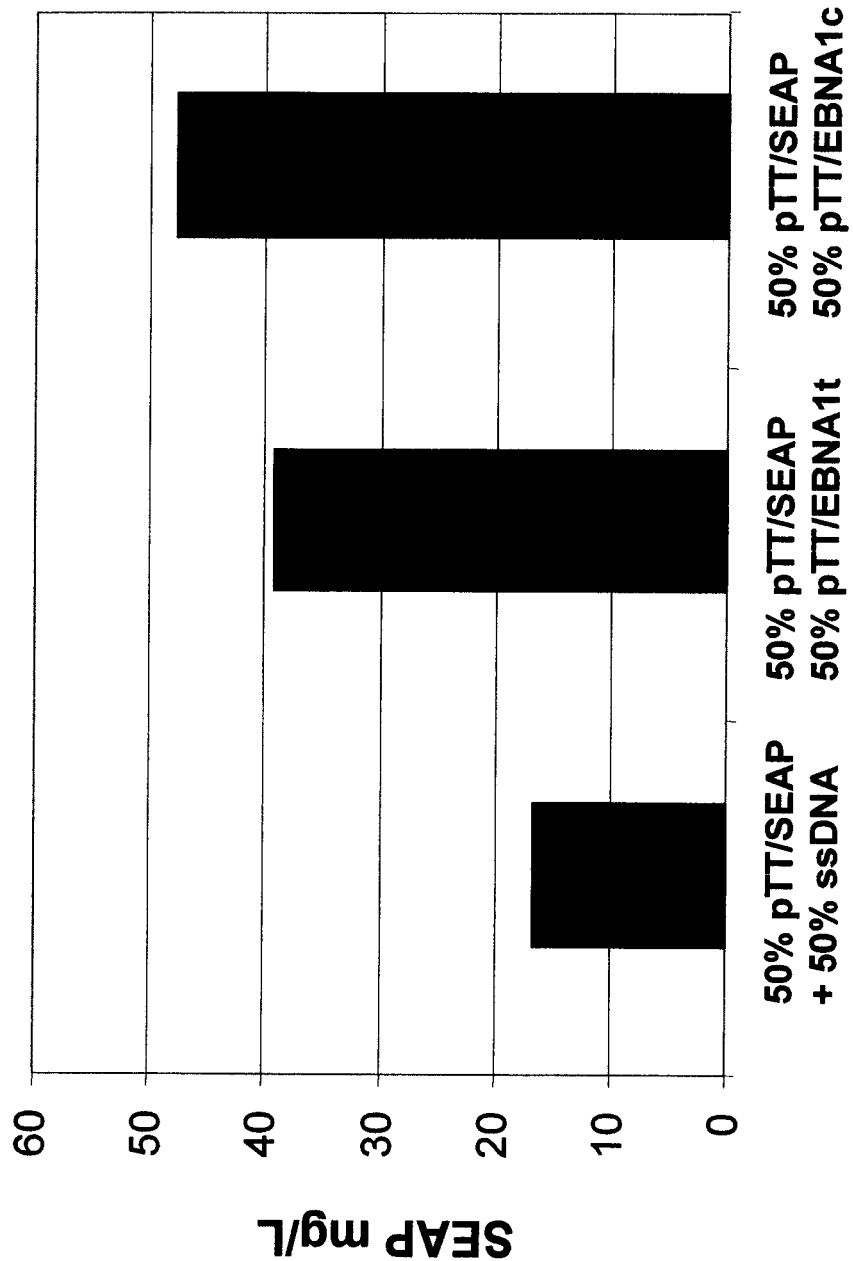
Figure 13: Effect of co-expressing EBNA1t or EBNA1c on transient SEAP expression in 293F cells.

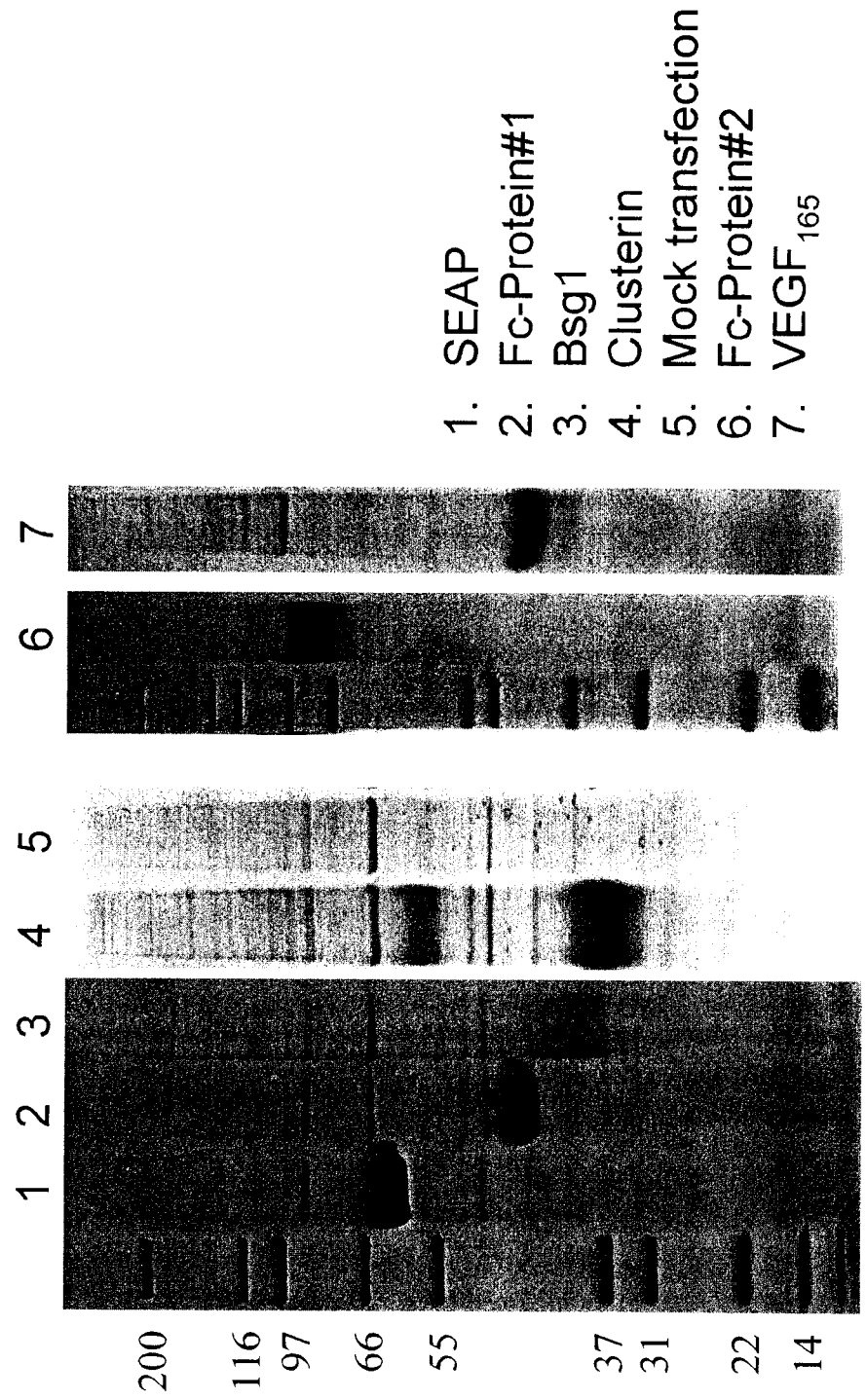
Figure 14: Transient expression of various secreted r-proteins in 293-6E cells using the pTT vector

EXPRESSION VECTORS CONTAINING A TRUNCATED EPSTEIN BARR NUCLEAR ANTIGEN 1 LACKING THE GLY-GLY-ALA DOMAIN FOR ENHANCED TRANSIENT GENE EXPRESSION

FIELD OF THE INVENTION

This invention relates to new mammalian cells and cell lines, especially CHO and 293 cell lines, which comprise expression vectors encoding truncated EBNA1 genes which enhance transient gene expression. The invention also relates to expression cassettes which include such truncated genes.

BACKGROUND OF THE INVENTION

Mammalian cells are an established expression system in the biotechnology industry for the production of recombinant proteins (r-proteins). In contrast to lower eukaryotes or prokaryotes, mammalian cells provide active r-proteins that possess relevant post-translational modifications. However, in order to obtain sufficient amount of protein for structure/activity analyses or high-throughput screenings, one needs to go through the long and tedious process of stable clone isolation and characterization. Protein production by large-scale transfection is an interesting alternative to the generation of stable clones as it allows the very fast generation of mg to gram quantities of r-protein within few days.

The use of vectors containing the Epstein-Barr virus (EBV) oriP in cell lines stably expressing EBV's EBNA1 protein, such as the HEK293-EBNA1 (293 E) cell line (ATCC#CRL-10852) significantly increases protein yield (Durocher et al., 2002). EBNA1 is a multi-functional protein that have been shown to positively regulate many viral promoters present on plasmid DNA when the oriP is present in cis (Reisman and Sugden, 1986).

The production of secreted r-protein often needs to be performed in serum-free medium in order to facilitate their purification. Adaptation of the 293E cell line to serum-free medium formulations is not straightforward and is rarely successful. To circumvent this problem, the generation of new 293-EBNA1 cell line from a serum-free medium adapted 293 cell line is preferable (Pham et al., 2003; Pham et al., 2005). However, these new cell lines do not always show optimal growth properties or high transfectabilities in serum-free medium. Also, the isolation of new clones stably expressing full-length EBNA1 is difficult as this protein seems to be cytotoxic to the cells.

Preliminary transient gene expression studies with the commercially available 293F cells adapted to the FreeStyle™ medium showed that this cell line has a good potential for the large-scale r-protein production in serum-free medium. Improvement of this cell line by stably expressing a less cytotoxic but functional EBNA1 protein is needed.

Kennedy, G. and Sugden, B. (2003) *EBNA-1, a Bifunctional Transcriptional Activator Molecular and Cellular Biology*, 23: 6901-6908 disclose that the ability of EBNA1 to activate transcription from both integrated and transfected templates can be inhibited by a derivative of EBNA1 lacking the amino acids required for activation from integrated templates (aa 65-89). We have found, against previous expectations, that truncations of these amino acids from EBNA1-coding nucleotide sequences can enhance transient gene expression in HEK293 cells to a level similar to EBNA1.

SUMMARY OF THE INVENTION

This invention relates to the unexpected discovery that nucleotide coding sequences coding for a truncated Epstein Barr Nuclear Antigen 1 (e.g. EBNA1t) protein (lacking the Gly-Gly-Ala domain), when in cells of mammalian origin, are associated with increased transient gene expression when compared with control cells. In addition, expression of this truncated EBNA1 gene is more stable and expressed at higher levels than expression of the full-length EBNA1 gene. This results in cell lines with better growth properties and with enhanced transient gene expression. Mammalian cell lines in general are contemplated and human embryonic kidney 293 cells, CHO cells and PER-C6™ cells are of particular interest. This invention also relates to a mammalian cell line such as a 293 cell line stably expressing a processed version of EBNA1t (e.g. 293-6E cells) also showing enhanced transient gene expression compared to EBNA1t, EBNA1 and control cell lines.

Preferably the transfected gene expression is performed in a cell line stably expressing truncated EBNA1. Alternatively, the transfected gene expression is associated with a transiently transfected EBNA1 gene. Also, preferably the EBNA1 nucleotide sequence is truncated to lack most of (i.e. more than 50%, preferably more than 75% and, in some embodiments, all) the Gly-Gly-Ala domain. Preferably the nucleotide sequence is less than 70% of a complete EBNA1 coding sequence, especially less than 50% of the complete EBNA1 coding sequence. Alternatively, or as well, one or more of the DNA linking regions LR1 and LR2 can be absent from the truncated sequence. One of the truncated sequences we have used lacks LR1 and we expect that an equivalent sequence lacking LR2 (with or without LR1 present) to serve a similar purpose. The nucleotide sequence can be included in an expression vector, such as a pTT vector or any other vectors containing a complete or partial Epstein Barr Virus (EBV) oriP sequence, allowing expression of the gene.

Stable cell lines including such expression vectors with truncated EBNA1 nucleotide coding sequences comprise an aspect of the invention.

According to one aspect of the invention, we provide new stable serum-free 293F-EBNA1 cell lines, including full-length of truncated versions of EBNA1.

The use of EBNA1t reduces the difficulty of obtaining stable clones (apparent deleterious effects of over-expressing the full-length EBNA1 protein). To our knowledge, no reports describing stable 293-EBNA1t cell lines exist. Also, by isolating and characterizing a stable 293F-EBNA1t cell line (clones 6E), we observed another new further truncated and functional form of EBNA1, of even shorter amino acid sequence length than EBNA1t (location of truncation not yet identified).

According to another aspect of the invention we provide a series of new truncated EBNA1t expressed proteins (including EBNA1c).

The following aspects of the invention are described in detail below.
1. The new 293FEt cell line, where Et is a truncated version of the EBNA1 protein e.g. EBNA1t described below and in the figures.
2. The new 293-6E cell line expressing a processed form of EBNA1t protein
3. The new truncated EBNA1 protein, EBNA1c consisting of LR2+NLS+DBD domains
4. Using transient EBNA1 (full-length or truncated) expression in trans to increase protein production in EBNA1 (full-length or truncated) and non-EBNA1 cell lines 5. The use of an EBNA1t or EBNA1c expression cassette in the pTT vector or other oriP-containing vectors (expression in cis) to increase protein production in EBNA1 and non-EBNA1 cells.
6. New truncated EBNA1 protein consisting of LR1+NLS+DBD domains.

The invention further relates to a process for in vitro production of a protein which process comprises:
(a) transfecting a mammalian cell with an expression vector coding for said protein, said mammalian cell having been transfected with a truncated EBNA1 expression vector of the invention;
(b) culturing a transfected cell resulting from (a) to yield said protein.

BRIEF DESCRIPTION OF THE DRAWINGS

In drawings which illustrate the invention,

FIG. 1 shows transient SEAP expression in 293F cells following co-transfection of various amounts of pTT/EBNA1t vector.

FIG. 2 shows stable or transient EBNA1 constructs expression in 293 cells.

FIG. 3 shows transient GFP expression in various 293F-EBNA1 clones or pools.

FIG. 4 shows a Western Blot analysis of EBNA1 expression in various 293F clones.

FIG. 5 shows transient human placental secreted alkaline phosphatase (SEAP) expression in various EBNA1 clones.

FIG. 6 shows the growth of various 293F-EBNA1 clones following transfection (hpt=hours post-transfection).

FIG. 7 shows the growth curve of 293-6E cells compared to 293F cell in 125 ml shaker flasks.

FIG. 8 shows the amino acid sequence of EBNA1 (SEQ ID NO: 1) with various parts of the sequence identified in the Figure.

FIG. 9 shows the amino acid sequence of full-length EBNA1 protein (SEQ ID NO: 1) and EBNA1t (underline) (SEQ ID NO: 2) and EBNA1c (bold) (SEQ ID NO: 3) truncated versions. The first amino acid of the new EBNA1c protein is a methionine (as indicated above the glycine residue).

FIG. 10 shows the schematic structure of various EBNA1 constructs.

FIG. 11 (A-C) shows DNA sequence of full-length EBNA1 (SEQ ID NO: 4), and truncated EBNA1 (EBNA1t (SEQ ID NO: 5) and EBNA1c (SEQ ID NO: 6)).

FIG. 12 shows transient EBNA1t and EBNA1c expression in 293F cells compared to 293F or 293-6E cells.

FIG. 13 shows the effect of co-expressing EBNA1t or EBNA1c on transient SEAP expression in 293F cells.

FIG. 14 shows examples of proteins transiently expressed in 293-6E cells.

DETAILED DESCRIPTION OF THE INVENTION

This invention relates to nucleotide coding sequences coding for a truncated Epstein Barr Nuclear Antigen 1 (EBNA1) protein which, when in cells of a mammalian cell line, are associated with increased transfected gene expression when compared with cells of a control cell line comprising a complete EBNA1 coding sequence. By "truncated" we mean a sequence which is less than the full EBNA1 nucleotide sequence. As shown in FIGS. 8 and 10 there are identified components of the full EBNA1 sequence. These include DNA Linking Regions 1 and 2, a Transcription activation domain, a Nuclear Localization Signal and a DNA Binding and Dimerization region. Truncated sequences of the invention preferably contain the DNA Binding and Dimerization region along with the Nuclear Localization Signal and one or more DNA Linking Regions. FIG. 1 shows that transient SEAP expression can be increased significantly by co-expression of EBNA1t protein. Similar increase can be observed using full length EBNA1 protein (not shown). This Figure also shows that transient SEAP expression does increase by augmenting EBNA1t expression. However, it seems that over expressing full-length EBNA1 is difficult to achieve in mammalian cells. This is illustrated in FIG. 2 where stable expression of full-length EBNA1 in the commercially available cell line HEK293-EBNA1 (formerly available at Invitrogen or available at ATCC #CRL-10852) or in our best SFE clone (SFE41; (Pham et al., 2003)) is significantly lower than in 293FEt bulks (lanes 6 and 7) or 293-6E cells (lanes 8 and 9). In addition, expression of full-length EBNA1 in 293F cells (bulk) in also very low (lanes 4 and 5). Note that while truncated forms of EBNA1 increases with time in these bulks (lanes 6 vs 7 and lanes 8 vs 9), expression of full length EBNA1 drops with time (lanes 4 vs 5), indicating that overexpression of full-length EBNA1 may have negative effects on cell physiology. Unexpectedly, a major and smaller form of EBNA1t was observed in clone 6E (lanes 8 and 9).

EBNAlt was amplified by PCR using forward (ACG-GAATTCGCCGCCACCATGTCTGACGAGGGGCCA) (SEQ ID NO:7) and reverse (GAGGAAGGGCAGGAGT-GAGAATTCCCT) (SEQ ID NO:8) primers and cloned at the EcoRI site of pIRES-Neo vector (Clontech). We made the 293FEt cell line (including the 293-6E clone) following transfection of 293F cells with the pIRES-EBNAlt-Neo vector and selection with 25 µg/ml geneticin. Stable clones were isolated by limiting dilution and clones selected based on EBNA1 expression using the rat monoclonal antibody 1H4 (Grasser et al., 1994). The 293-6E clone was deposited on Mar. 15, 2005, as a Budapest Treaty deposit in the International Depositary Authority of Canada, National Microbiology Laboratory, Health Canada, 1015 Arlington Street, Winnipeg, Manitoba Canada R3E 3R2, as accession number 150305-01.

FIG. 1 shows that expressing EBNA1t increases transient SEAP expression in a dose-dependent manner. 293F cells were transfected with 100% pTT-SEAP vector (CTRL) or with mixtures of 99 to 60% pTT-SEAP and 1 to 40% of pTT-EBNA1t respectively. With 60% pTT-SEAP and 40% pTT-EBNA1t, the expression level of SEAP was increased by 3-fold over control.

FIG. 2 shows EBNA1 expression levels in various stable HEK293 cell lines or following transient transfection. Stable expression of full-length EBNA1 in HEK293-EBNA1 cell line (lane 1) and 293-SFE cell line (lane 2). Lane 3: 293F cells (no EBNA1 expression). Expression of full-length EBNA1 in 293F cells following transfection and G418 selection for 2 months (lane 4) and 4 months (lane 5). Note that expression of full-length EBNA1 decreases with time in this non-clonal cell population. Expression of truncated EBNA1 (EBNA1t) in 293F cells following transfection and G418 selection for 2 months (lane 6) and 4 months (lane 7). Note that expression of EBNA1t increases with time in this non-clonal cell population. Expression of the new form of EBNA1t in clone 6E derived from 293F-EBNA1t after 4 months in culture in the presence of G418 and 1% serum (lane 8) or G418 in serum-free medium (lane 9). Transient expression of full-length EBNA1 (lane 10) or EBNA1t (lane 11) in 293F cells.

The precise nature of the new EBNA1t protein remains to be solved. Detection of EBNA1 was performed using a rat monoclonal antibody (clone 1H4). The two bands seen at Mr 200 and above are not-specific.

FIG. 3 shows transient GFP expression in various EBNA1 cell lines. Cells (cultured for 3 months under G418 selection following transfection) were transfected with pTT-GFP and GFP expression was measured 3 days later by flow cytometry. The 293F-EBNA1t clone 6E shows the highest GFP expression. Transfection efficiency was between 40% and 65% for all clones.

FIG. 4 shows EBNA1 expression levels in various 293 clones. All clones were cultured in the presence of 25 µg/ml geneticin. Expression of EBNA1 in clone 6A can be detected with longer exposure time.

FIG. 5 shows that when various 293F-EBNA1 stable clones were transfected with pTT/SEAP, the clones expressing truncated EBNA1 coding sequences showed enhanced SEAP expression when measured 5 days later (clones 6E, 11 and 13) when compared to clones expressing the full length (clones 1A and 2B) or another uncharacterized truncated form of EBNA1 (clone 6A). In the context of this invention, SEAP is an example of a recombinant protein. Genetic material coding for a protein or polypeptide of choice can be used in place of SEAP coding sequences and, indeed, this is an aim of this invention (see FIG. 14 for additional examples).

FIG. 6 shows that cell growth and viability does not appear to be affected when truncated EBNA1 nucleotide sequences are stably overexpressed. Cells were fed with 0.5% TN1 24 hpt (Pham et al., 2005) and counted 6 days after transfection.

FIG. 7 shows the growth characteristic of the 293FEt-clone 6E (lower panel) compared to the parental 293F cell line (upper panel). Maximum viable cell density is about $3.5 \times 10^6$ cells/ml for the clone 6E compared to $4.2 \times 10^6$ cells/ml for the 293F cell line.

FIG. 8, FIG. 9, FIG. 10 and FIG. 11 are best reviewed together. They show the amino acid sequence and schematic structure of EBNA1 constructs and the relationship to the EBNA1 DNA sequences (FIGS. 11A-C).

FIG. 8 shows the EBNA1 full length protein (641 aa, 56.4 kDa) (Accession number: NC_001345) with its main features. FIG. 9 highlights the differences between EBNA1, EBNA1t and EBNA1c and the amino acid level. EBNA1t truncated protein (underline: 417 aa, 42.5 kDa) and EBNA1c further truncated protein (bold: 306 aa, 32.5 kDa). The first amino acid of the new EBNA1c protein is a Methionine (as indicated above the Glycine residue).

FIG. 12 contrasts transient expression of two truncated EBNA1 constructs with 293F and 293-6E cells. Cells were transfected with pTT/EBNA1t or pTT/EBNA1c vectors and EBNA1 expression was detected 3 days later by Western blot. Non-transfected 293F cells and 293-6E cells are also shown as controls.

FIG. 13 shows 293F cells co-transfected with pTT/SEAP and pTT/EBNA1 constructs. 293F cells were co-transfected with a mixture of 50% pTT-SEAP vector with pTT/EBNA1t, 50% pTT/EBNA1c, or 50% salmon sperm DNA (stuffer DNA). SEAP expression was measured 5 days later.

FIG. 14 shows examples of proteins transiently expressed in 293-6E cells. 293-6E cells were transfected with pTT vectors encoding various secreted proteins and culture medium (20 microliters) was harvested 5 days after transfection and analyzed by SDS-PAGE and Coomassie staining.

REFERENCE LIST

Durocher, Y., Perret, S., and Kamen, A., 2002. High-level and high-throughput recombinant protein production by transient transfection of suspension-growing human 293-EBNA1 cells. Nucleic Acids Res. 30, E9.

Grasser, F. A., Murray, P. G., Kremmer, E., Klein, K., Remberger, K., Feiden, W., Reynolds, G., Niedobitek, G., Young, L. S., and Mueller-Lantzsch, N., 1994. Monoclonal antibodies directed against the Epstein-Barr virus-encoded nuclear antigen 1 (EBNA1): immunohistologic detection of EBNA1 in the malignant cells of Hodgkin's disease. Blood 84, 3792-3798.

Pham, P. L., Perret, S., Cass, B., Carpentier, E., St-Laurent, G., Bisson, L., Kamen, A., and Durocher, Y., 2005. Transient gene expression in HEK293 cells: peptone addition posttransfection improves recombinant protein synthesis. Biotechnol. Bioeng. 90, 332-344.

Pham, P. L., Perret, S., Doan, H. C., Cass, B., St-Laurent, G., Kamen, A., and Durocher, Y., 2003. Large-scale transient transfection of serum-free suspension-growing HEK293 EBNA1 cells: peptone additives improve cell growth and transfection efficiency. Biotechnol. Bioeng. 84, 332-342.

Reisman, D. and Sugden, B., 1986. trans activation of an Epstein-Barr viral transcriptional enhancer by the Epstein-Barr viral nuclear antigen 1. Mol. Cell Biol. 6, 3838-3846.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A mammalian cell line that stably expresses a truncated Epstein Barr Nuclear Antigen 1 (EBNA1) protein, which cell line is the 293-6E cell line deposited at the International Depositary Authority of Canada under accession number 150305-01.

2. A process for transient in vitro production of a recombinant protein, which process comprises:
   (a) transfecting a mammalian cell line in accordance with claim 1 with an expression vector coding for a recombinant protein; and
   (b) culturing the transfected cell resulting from (a) to yield said recombinant protein.

3. A process in accordance with claim 2, wherein said expression vector further includes a complete or partial Epstein Barr Virus (EBV) oriP sequence.

* * * * *

SEQUENCE LISTING

```
<160> NUMBER OF SEQ ID NOS: 8

<210> SEQ ID NO 1
<211> LENGTH: 641
<212> TYPE: PRT
<213> ORGANISM: Epstein Barr Virus
<220> FEATURE:
<221> NAME/KEY: MISC_FEATURE
<223> OTHER INFORMATION: EBNA1 Full Length Protein Sequence

<400> SEQUENCE: 1

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30
```

-continued

```
Arg Arg Gly Gly Asp Asn His Gly Arg Gly Arg Gly Arg Gly
            35                  40                  45
Arg Gly Gly Gly Arg Pro Gly Ala Pro Gly Gly Gly Ser Gly Pro
 50                  55                  60
Arg His Arg Asp Gly Val Arg Arg Pro Gln Lys Arg Pro Ser Cys Ile
 65                  70                  75                  80
Gly Cys Lys Gly Thr His Gly Gly Thr Gly Ala Gly Ala Gly Ala Gly
                     85                  90                  95
Gly Ala Gly Ala Gly Gly Ala Gly Ala Gly Gly Ala Gly Ala Gly
                100                 105                 110
Gly Gly Ala Gly Gly Ala Gly Gly Ala Gly Gly Ala Gly Ala Gly Gly
            115                 120                 125
Gly Ala Gly Ala Gly Gly Ala Gly Gly Ala Gly Gly Ala Gly Ala
            130                 135                 140
Gly Gly Gly Ala Gly Ala Gly Gly Ala Gly Gly Ala Gly Ala Gly
 145                 150                 155                 160
Gly Gly Ala Gly Gly Ala Gly Gly Ala Gly Ala Gly Gly Ala Gly
                165                 170                 175
Ala Gly Gly Gly Ala Gly Gly Ala Gly Ala Gly Gly Ala Gly Gly
            180                 185                 190
Ala Gly Gly Ala Gly Ala Gly Gly Ala Gly Ala Gly Gly Ala Gly
            195                 200                 205
Gly Ala Gly Gly Ala Gly Ala Gly Ala Gly Ala Gly Gly Gly Ala
 210                 215                 220
Gly Gly Ala Gly Gly Ala Gly Ala Gly Gly Ala Gly Ala Gly Gly Ala
 225                 230                 235                 240
Gly Ala Gly Gly Ala Gly Ala Gly Gly Ala Gly Ala Gly Ala Gly
                245                 250                 255
Gly Ala Gly Gly Ala Gly Ala Gly Gly Ala Gly Ala Gly Ala Gly
                260                 265                 270
Gly Gly Ala Gly Gly Ala Gly Ala Gly Gly Ala Gly Ala Gly Gly Ala Gly
            275                 280                 285
Ala Gly Gly Ala Gly Gly Ala Gly Ala Gly Gly Ala Gly Gly Ala Gly
 290                 295                 300
Ala Gly Gly Ala Gly Gly Ala Gly Ala Gly Gly Ala Gly Ala Gly
 305                 310                 315                 320
Gly Ala Gly Ala Gly Gly Gly Gly Arg Gly Arg Gly Ser Gly Gly
                325                 330                 335
Arg Gly Arg Gly Ser Gly Gly Gly Arg Gly Gly Gly Ser Gly Gly
            340                 345                 350
Arg Arg Gly Arg Gly Arg Glu Arg Ala Arg Gly Gly Ser Arg Glu Arg
 355                 360                 365
Ala Arg Gly Arg Gly Arg Gly Arg Gly Glu Lys Arg Pro Arg Ser Pro
 370                 375                 380
Ser Ser Gln Ser Ser Ser Ser Gly Ser Pro Pro Arg Arg Pro Pro Pro
 385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
                420                 425                 430
Ala Ile Glu Gln Gly Pro Ala Asp Asp Pro Gly Glu Gly Pro Ser Thr
            435                 440                 445
Gly Pro Arg Gly Gln Gly Asp Gly Gly Arg Arg Lys Lys Gly Gly Trp
 450                 455                 460
```

```
Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
                515                 520                 525

Pro Gln Cys Arg Leu Thr Pro Leu Ser Arg Leu Pro Phe Gly Met Ala
530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
                580                 585                 590

Ile Arg Val Thr Val Cys Ser Phe Asp Asp Gly Val Asp Leu Pro Pro
                595                 600                 605

Trp Phe Pro Pro Met Val Glu Gly Ala Ala Ala Glu Gly Asp Asp Gly
610                 615                 620

Asp Asp Gly Asp Glu Gly Gly Asp Gly Asp Glu Gly Glu Glu Gly Gln
625                 630                 635                 640

Glu

<210> SEQ ID NO 2
<211> LENGTH: 417
<212> TYPE: PRT
<213> ORGANISM: Epstein Barr Virus
<220> FEATURE:
<221> NAME/KEY: MISC_FEATURE
<223> OTHER INFORMATION: EBNA1t Truncated Protein Sequence

<400> SEQUENCE: 2

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
                20                  25                  30

Arg Arg Gly Gly Asp Asn His Gly Arg Gly Arg Gly Arg Gly Arg Gly
            35                  40                  45

Arg Gly Gly Gly Arg Pro Gly Ala Pro Gly Gly Ser Gly Ser Gly Pro
        50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Gly Gly Arg Gly Arg Gly Gly Ser Gly Gly
            100                 105                 110

Arg Gly Arg Gly Gly Ser Gly Gly Arg Gly Gly Ser Gly Gly
        115                 120                 125

Arg Arg Gly Arg Gly Arg Glu Arg Ala Arg Gly Gly Ser Arg Glu Arg
    130                 135                 140

Ala Arg Gly Arg Gly Arg Gly Arg Gly Glu Lys Arg Pro Arg Ser Pro
145                 150                 155                 160

Ser Ser Gln Ser Ser Ser Ser Gly Ser Pro Pro Arg Arg Pro Pro Pro
                165                 170                 175
```

```
Gly Arg Arg Pro Phe Phe His Pro Val Gly Glu Ala Asp Tyr Phe Glu
            180                 185                 190
Tyr His Gln Glu Gly Gly Pro Asp Gly Glu Pro Asp Val Pro Pro Gly
        195                 200                 205
Ala Ile Glu Gln Gly Pro Ala Asp Asp Pro Gly Glu Gly Pro Ser Thr
    210                 215                 220
Gly Pro Arg Gly Gln Gly Asp Gly Gly Arg Arg Lys Lys Gly Gly Trp
225                 230                 235                 240
Phe Gly Lys His Arg Gly Gln Gly Gly Ser Asn Pro Lys Phe Glu Asn
                245                 250                 255
Ile Ala Glu Gly Leu Arg Ala Leu Leu Ala Arg Ser His Val Glu Arg
            260                 265                 270
Thr Thr Asp Glu Gly Thr Trp Val Ala Gly Val Phe Val Tyr Gly Gly
        275                 280                 285
Ser Lys Thr Ser Leu Tyr Asn Leu Arg Arg Gly Thr Ala Leu Ala Ile
    290                 295                 300
Pro Gln Cys Arg Leu Thr Pro Leu Ser Arg Leu Pro Phe Gly Met Ala
305                 310                 315                 320
Pro Gly Pro Gly Pro Gln Pro Gly Pro Leu Arg Glu Ser Ile Val Cys
                325                 330                 335
Tyr Phe Met Val Phe Leu Gln Thr His Ile Phe Ala Glu Val Leu Lys
            340                 345                 350
Asp Ala Ile Lys Asp Leu Val Met Thr Lys Pro Ala Pro Thr Cys Asn
        355                 360                 365
Ile Arg Val Thr Val Cys Ser Phe Asp Asp Gly Val Asp Leu Pro Pro
    370                 375                 380
Trp Phe Pro Pro Met Val Glu Gly Ala Ala Glu Gly Asp Asp
385                 390                 395                 400
Asp Asp Gly Asp Glu Gly Gly Asp Gly Asp Glu Gly Glu Gly Gly Gln
                405                 410                 415
Glu

<210> SEQ ID NO 3
<211> LENGTH: 306
<212> TYPE: PRT
<213> ORGANISM: Epstein Barr Virus
<220> FEATURE:
<221> NAME/KEY: MISC_FEATURE
<223> OTHER INFORMATION: EBNA1c Truncated Protein Sequence

<400> SEQUENCE: 3

Met Arg Gly Arg Gly Gly Ser Gly Gly Arg Gly Arg Gly Gly Ser Gly
1               5                   10                  15
Gly Arg Arg Gly Arg Gly Arg Glu Arg Ala Arg Gly Gly Ser Arg Glu
            20                  25                  30
Arg Ala Arg Gly Arg Gly Arg Gly Arg Gly Glu Lys Arg Pro Arg Ser
        35                  40                  45
Pro Ser Ser Gln Ser Ser Ser Ser Gly Ser Pro Pro Arg Arg Pro Pro
    50                  55                  60
Pro Gly Arg Arg Pro Phe Phe His Pro Val Gly Glu Ala Asp Tyr Phe
65                  70                  75                  80
Glu Tyr His Gln Glu Gly Gly Pro Asp Gly Glu Pro Asp Val Pro Pro
                85                  90                  95
Gly Ala Ile Glu Gln Gly Pro Ala Asp Asp Pro Gly Glu Gly Pro Ser
            100                 105                 110
```

```
Thr Gly Pro Arg Gly Gln Gly Asp Gly Gly Arg Arg Lys Lys Gly Gly
            115                 120                 125
Trp Phe Gly Lys His Arg Gly Gln Gly Gly Ser Asn Pro Lys Phe Glu
        130                 135                 140
Asn Ile Ala Glu Gly Leu Arg Ala Leu Leu Ala Arg Ser His Val Glu
145                 150                 155                 160
Arg Thr Thr Asp Glu Gly Thr Trp Val Ala Gly Val Phe Val Tyr Gly
                165                 170                 175
Gly Ser Lys Thr Ser Leu Tyr Asn Leu Arg Arg Gly Thr Ala Leu Ala
            180                 185                 190
Ile Pro Gln Cys Arg Leu Thr Pro Leu Ser Arg Leu Pro Phe Gly Met
        195                 200                 205
Ala Pro Gly Pro Gly Pro Gln Pro Gly Pro Leu Arg Glu Ser Ile Val
210                 215                 220
Cys Tyr Phe Met Val Phe Leu Gln Thr His Ile Phe Ala Glu Val Leu
225                 230                 235                 240
Lys Asp Ala Ile Lys Asp Leu Val Met Thr Lys Pro Ala Pro Thr Cys
                245                 250                 255
Asn Ile Arg Val Thr Val Cys Ser Phe Asp Asp Gly Val Asp Leu Pro
            260                 265                 270
Pro Trp Phe Pro Pro Met Val Glu Gly Ala Ala Ala Glu Gly Asp Asp
        275                 280                 285
Gly Asp Asp Gly Asp Glu Gly Gly Asp Gly Asp Glu Gly Glu Glu Gly
290                 295                 300
Gln Glu
305

<210> SEQ ID NO 4
<211> LENGTH: 1926
<212> TYPE: DNA
<213> ORGANISM: Epstein Barr Virus
<220> FEATURE:
<221> NAME/KEY: misc_feature
<223> OTHER INFORMATION: EBNA1 Full Length DNA Sequence

<400> SEQUENCE: 4
atgtctgacg aggggccagg tacaggacct ggaaatggcc taggagagaa gggagacaca      60
tctggaccag aaggctccgg cggcagtgga cctcaaagaa gaggggtga taaccatgga     120 cgaggacggg gaagaggacg aggacgagga ggcggaagac caggagcccc gggcggctca     180
ggatcagggc caagacatag agatggtgtc cggagacccc aaaaacgtcc aagttgcatt     240
ggctgcaaag gacccacgg tggaacagga gcaggagcag gagcgggagg ggcaggagca     300
ggaggggcag gagcaggagg aggggcagga gcaggaggag gggcaggagg ggcaggaggg     360
gcaggagggg caggagcagg aggggggca ggagcaggag gaggggcagg aggggcagga     420
ggggcaggag caggagagg ggcaggagca ggaggagggg caggagggc aggagcagga     480 ggaggggcag gaggggcagg aggggcagga gcaggaggag gggcaggagc aggaggaggg     540
gcaggagggg caggagcagg aggggggca ggaggggcag gaggggcagg agcaggagga     600
ggggcaggag caggaggggc aggaggggca ggaggggcag gagcaggagg ggcaggagca     660
ggaggagggg caggaggggc aggaggggca ggagcaggag ggcaggagc aggaggggca     720 ggagcaggag ggcaggagc aggaggggca ggaggggcag gagcaggagg ggcaggaggg     780
gcaggagcag gaggggcagg aggggcagga gcaggaggag gggcaggagg ggcaggagca     840
ggaggagggg caggaggggc aggagcagga ggggcaggag gggcaggagc aggaggggca     900
```

| | |
|---|---|
| ggaggggcag gagcaggagg ggcaggaggg gcaggagcag gaggaggggc aggagcagga | 960 |
| ggggcaggag caggaggtgg aggccggggt cgaggaggca gtggaggccg gggtcgagga | 1020 |
| ggtagtggag gccggggtcg aggaggtagt ggaggccgcc ggggtagagg acgtgaaaga | 1080 |
| gccagggggg gaagtcgtga aagagccagg gggagaggtc gtggacgtgg agaaaagagg | 1140 |
| cccaggagtc ccagtagtca gtcatcatca tccgggtctc caccgcgcag gccccctcca | 1200 |
| ggtagaaggc cattttttcca ccctgtaggg gaagccgatt attttgaata ccaccaagaa | 1260 |
| ggtggcccag atggtgagcc tgacgtgccc ccgggagcga tagagcaggg ccccgcagat | 1320 |
| gacccaggag aaggcccaag cactggaccc ggggtcagg gtgatggagg caggcgcaaa | 1380 |
| aaaggagggt ggtttggaaa gcatcgtggt caaggaggtt ccaacccgaa atttgagaac | 1440 |
| attgcagaag gtttaagagc tctcctggct aggagtcacg tagaaaggac taccgacgaa | 1500 |
| ggaacttggg tcgccggtgt gttcgtatat ggaggtagta agacctccct ttacaaccta | 1560 |
| aggcgaggaa ctgcccttgc tattccacaa tgtcgtctta caccattgag tcgtctcccc | 1620 |
| tttggaatgg cccctggacc cggcccacaa cctggcccgc taagggagtc cattgtctgt | 1680 |
| tatttcatgg tcttttttaca aactcatata tttgctgagg ttttgaagga tgcgattaag | 1740 |
| gaccttgtta tgacaaagcc cgctcctacc tgcaatatca gggtgactgt gtgcagcttt | 1800 |
| gacgatggag tagatttgcc tccctggttt ccacctatgg tggaaggggc tgccgcggag | 1860 |
| ggtgatgacg gagatgacgg agatgaagga ggtgatggag atgagggtga ggaagggcag | 1920 |
| gagtga | 1926 |

```
<210> SEQ ID NO 5
<211> LENGTH: 1254
<212> TYPE: DNA
<213> ORGANISM: Epstein Barr Virus
<220> FEATURE:
<221> NAME/KEY: misc_feature
<223> OTHER INFORMATION: EBNA1t Truncated DNASequence

<400> SEQUENCE: 5
```

| | |
|---|---|
| atgtctgacg aggggccagg tacaggacct ggaaatggcc taggagagaa gggagacaca | 60 |
| tctggaccag aaggctccgg cggcagtgga cctcaaagaa gaggggtga taaccatgga | 120 |
| cgaggacggg gaagaggacg aggacgagga ggcggaagac caggagcccc gggcggctca | 180 |
| ggatcagggc caagacatag agatggtgtc cggagacccc aaaaacgtcc aagttgcatt | 240 |
| ggctgcaaag ggacccacgg tggaacagga gcaggagcag gagcgggagg ggcaggagca | 300 |
| ggaggtggag gccggggtcg aggaggcagt ggaggccggg gtcgaggagg tagtggaggc | 360 |
| cggggtcgag gaggtagtgg aggccgccgg ggtagaggac gtgaaagagc caggggggga | 420 |
| agtcgtgaaa gagccagggg gagaggtcgt ggacgtggag aaaagaggcc caggagtccc | 480 |
| agtagtcagt catcatcatc cgggtctcca ccgcgcaggc cccctccagg tagaaggcca | 540 |
| tttttccacc ctgtagggga agccgattat tttgaatacc accaagaagg tggcccagat | 600 |
| ggtgagcctg acgtgccccc gggagcgata gagcagggcc ccgcagatga cccaggagaa | 660 |
| ggcccaagca ctggacccg ggtcaggt gatggaggca ggcgcaaaaa aggagggtgg | 720 |
| tttggaaagc atcgtggtca aggaggttcc aacccgaaat ttgagaacat tgcagaaggt | 780 |
| ttaagagctc tcctggctag gagtcacgta gaaaggacta ccgacgaagg aacttgggtc | 840 |
| gccggtgtgt tcgtatatgg aggtagtaag acctcccttt acaacctaag gcgaggaact | 900 |
| gcccttgcta ttccacaatg tcgtcttaca ccattgagtc gtctcccctt tggaatggcc | 960 |

```
cctggacccg gcccacaacc tggcccgcta agggagtcca ttgtctgtta tttcatggtc    1020
tttttacaaa ctcatatatt tgctgaggtt ttgaaggatg cgattaagga ccttgttatg    1080
acaaagcccg ctcctacctg caatatcagg gtgactgtgt gcagctttga cgatggagta    1140
gatttgcctc cctggtttcc acctatggtg aaggggctg ccgcggaggg tgatgacgga     1200
gatgacggag atgaaggagg tgatggagat gagggtgagg aagggcagga gtga          1254
```

<210> SEQ ID NO 6
<211> LENGTH: 921
<212> TYPE: DNA
<213> ORGANISM: Epstein Barr Virus
<220> FEATURE:
<221> NAME/KEY: misc_feature
<223> OTHER INFORMATION: EBNA1c Truncated DNA Sequence

<400> SEQUENCE: 6

```
atgcgggtc gaggaggtag tggaggccgg ggtcgaggag gtagtggagg ccgccggggt     60
agaggacgtg aaagagccag ggggggaagt cgtgaaagac ccaggggag aggtcgtgga     120 cgtggagaaa agaggcccag gagtcccagt agtcagtcat catcatccgg gtctccaccg    180
cgcaggcccc ctccaggtag aaggccattt ttccaccctg taggggaagc cgattatttt    240
gaataccacc aagaaggtgg cccagatggt gagcctgacg tgccccgg agcgatagag      300 cagggcccg cagatgaccc aggagaaggc ccaagcactg accccgggg tcagggtgat      360 ggaggcaggc gcaaaaaagg agggtggttt ggaaagcatc gtggtcaagg aggttccaac    420
ccgaaatttg agaacattgc agaaggttta agagctctcc tggctaggag tcacgtagaa    480
aggactaccg acgaaggaac ttgggtcgcc ggtgtgttcg tatatggagg tagtaagacc    540 tcccttaca acctaaggcg aggaactgcc cttgctattc cacaatgtcg tcttacacca    600
ttgagtcgtc tcccctttgg aatggcccct ggacccggcc cacaacctgg cccgctaagg    660
gagtccattg tctgttattt catggtcttt ttacaaactc atatattgc tgaggttttg    720 aaggatgcga ttaaggacct tgttatgaca aagcccgctc ctacctgcaa tatcaggtg    780 actgtgtgca gctttgacga tggagtagat ttgcctccct ggtttccacc tatggtggaa    840
ggggctgccg cggagggtga tgacggagat gacggagatg aaggaggtga tggagatgag    900
ggtgaggaag ggcaggagtg a                                              921
```

<210> SEQ ID NO 7
<211> LENGTH: 36
<212> TYPE: DNA
<213> ORGANISM: Artificial
<220> FEATURE:
<223> OTHER INFORMATION: Forward Primer

<400> SEQUENCE: 7

```
acggaattcg ccgccaccat gtctgacgag gggcca                              36
```

<210> SEQ ID NO 8
<211> LENGTH: 27
<212> TYPE: DNA
<213> ORGANISM: Artificial
<220> FEATURE:
<223> OTHER INFORMATION: Reverse Primer

<400> SEQUENCE: 8

```
gaggaagggc aggagtgaga attccct                                        27
```